United States Patent [19]

John

[11] Patent Number: 5,699,808
[45] Date of Patent: Dec. 23, 1997

[54] EEG OPERATIVE AND POST-OPERATIVE PATIENT MONITORING SYSTEM AND METHOD

[75] Inventor: Erwin Roy John, Mamaroneck, N.Y.

[73] Assignee: New York University, New York, N.Y.

[21] Appl. No.: 612,094

[22] Filed: Mar. 7, 1996

Related U.S. Application Data

[63] Continuation of Ser. No. 192,836, Feb. 7, 1994, abandoned.

[51] Int. Cl.$^6$ ............................................... A61B 5/004
[52] U.S. Cl. ............................................... 128/731; 128/670
[58] Field of Search ............................... 128/670, 731, 128/732

[56] References Cited

U.S. PATENT DOCUMENTS

| 4,705,049 | 11/1987 | John ....................... | 128/731 |
| 4,846,190 | 7/1989 | John ....................... | 128/731 |
| 4,869,264 | 9/1989 | Silberstein ................ | 128/731 |

OTHER PUBLICATIONS

John et al., "Intraoperative Monitoring with Evoked Potentials", Advanced Technology in Neurosurgery, Springer-Verlag Berlin Heidelberg, 1988, pp. 64–83.

*Primary Examiner*—Lee S. Cohen
*Assistant Examiner*—Bryan K. Yarnell
*Attorney, Agent, or Firm*—Eliot S. Gerber

[57] ABSTRACT

An electrocephalograph (EEG) system and method is provided to monitor patients during and after medical operations. An anesthesiologist administers sufficient anesthetics to cause the patient to attain the desired plane of anesthesia. The patient's brain waves, both ongoing and evoked by stimuli, are amplified, digitized and recorded. That preoperative set of brain wave data is compared to a set of the patient's brain wave data obtained during the operation in order to determine if additional, or less, anesthesia is required, paying particular attention to the relative power in the theta band, as an indication of brain blood flow, and prolongations of the latency periods under brain stem stimuli, as an indication of the patient's ability to feel pain.

7 Claims, 3 Drawing Sheets

1

EEG OPERATIVE AND POST-OPERATIVE PATIENT MONITORING SYSTEM AND METHOD

This application is a continuation of Ser. No. 08/192,836, filed Feb. 7, 1994, now abandoned.

FIELD OF THE INVENTION

The present invention relates to medical systems and methods and more particularly to an electroencephalograph (EEG) based system for patient monitoring of anesthesia during surgical operations and in recovery and intensive care.

BACKGROUND OF THE INVENTION

At the present time anesthetics (drugs which induce loss of sensation) are often used for surgical operations. A general anesthetic should cause a progressive depression of the central nervous system and cause the patient to lose consciousness. In contrast, a local anesthetic will affect sensation at the region to which it is applied.

Generally, the patient, prior to the operation, is anesthetized by a specialized medical practitioner ("anesthesiologist") who administers one or more volatile liquids or gases, such as nitrous oxide, ethylene, cyclopropane, ether, chloroform, halothane, etc. Alternatively, non-volatile drugs may be administered by injection or intravenous infusion, such drugs including pentothal, evipal and procaine.

Some of the objectives of a correctly administered general anesthetic are as follows:

First, the patient should be sufficiently anesthetized so that his/her movements are blocked. If the patient's movements are not sufficiently blocked, the patient may begin to "twitch" (involuntary muscle reflexes) during the operation, which may move or disturb the operating field (area being operated upon). Such blockage of movement occurs with a paralysis of the central nervous system after the sensory cortex is suppressed. This paralysis affects, in order, the basal ganglia, the cerebellum and then the spinal cord. The medulla, which controls respiratory, cardiac and vasomotor centers, is not affected by the anesthetic.

Secondly, the patient should be sufficiently unconscious so as to feel no pain and be unaware of the operation. Patients have sued for medical malpractice because they felt pain during the operation or were aware of the surgical procedure.

Thirdly, the anesthesia should not be administered in an amount so as to lower blood pressure to the point where blood flow to the brain may be reduced to a dangerous extent (generally below 50 mm Hg for mean arterial pressure (MAP)), i.e., cause cerebral ischemia and hypoxia. For example, if the blood pressure is too low for over 10 minutes, the patient may not regain consciousness.

A skilled anesthesiologist may monitor the vital signals (breathing, blood pressure, etc.) of the patient to determine if more, or less, anesthetic is required. Often he/she looks into the patient's eyes to determine the extent of the dilation of the pupils as an indication of the level (depth) of the effect of the anesthesia (called "plane of anesthesia"). However, there may be a number of problems with such complete reliance on the skill and attention of the anesthesiologist. In some operations, such as some heart surgery, the head is covered so that the patient's eyes cannot be viewed. Some operations may be prolonged, for example, 10 to 15 hours, so the attention of the anesthesia nurse or anesthesiologist may flag or fail.

It has been suggested that some of these problems would be avoided by having a computer system determine the best anesthetic mix and the amount of each anesthetic based on the patient's sex, age, weight, physical condition and the type of operation. However, it is believed that such a computer determination would not be successful due to the great diversity of individuals in response to different anesthetics.

The inventor's prior U.S. Pat. No. 4,557,270, entitled "Electroencephalographic System For Intra-Operative Open-Heart Surgery", incorporated by reference herein, describes an electroencephalograph (EEG) system used intra-operatively in cardiovascular (open-heart) operations using a heart-lung machine (cardiopulmonary by-pass) such as heart valve replacement surgery. That system, called "CIMON" (Cardiovascular Intraoperative Monitor) is presently being sold by Cadwell Laboratories, Kennewick, Wash., and has been successfully used in many heart operations. However, the CIMON system, with its attention to the heart-pump rate, etc., is not used in general surgery.

In Chamoun U.S. Pat. No. 5,010,891 EEG potentials from a group of healthy surgical patients are recorded (col. 14, lines 32–34). A "reference array" is obtained of the most significant locations and an "autobispectral density index" is defined based on the recordings from a normal group. Each normal group index is then compared to the index of the patient under review. However, as explained above, the comparison of patients with a normal group is not believed to provide reliable information in the surgical context of determining if a patient will be sufficiently anesthetized.

SUMMARY OF THE INVENTION

In accordance with the present invention, an EEG system and method is provided to help the anesthesiologist monitor a patient during an operation. The same, or similar, system may be used postoperatively in the recovery room and may be used to monitor patients in an Intensive Care Unit (ICU).

In the context of a surgical operation, a set of preferably six EEG electrodes are removably fastened to the scalp of the patient. The anesthesiologist will administer an anesthetic, generally gas, to the patient until the patient has attained the desired plane of anesthesia, in the opinion of the anesthesiologist, based upon the patient's vital signals and other signs, including eye pupil dilation.

The patient's brain waves, at that point, are collected, analyzed and become the norm ("reference"). In theory, if the patient's brain waves are correctly analyzed and remain, during the operation, within a band ("reference band") close to the reference, the patient should remain at the same desired plane of anesthesia. Depending on the direction of movement of the analyzed brain waves, if outside of the reference band, either more or less anesthesia should be administered, or oxygen should be administered.

It has been found that the amount of relative brain wave power in the theta band (3.5–7.5 Hz) is inversely proportional to cerebral blood flow. When brain blood flow drops, relative theta brain wave power will increase, indicating that a suitable adjustment, such as added oxygen, may be required. The six EEG electrodes will detect increased relative Theta power reflecting local lack of blood in the six regions near the electrodes, which are perfused by the six major blood arteries to the brain, so that any local oxygen deficiency may be detected.

It has also been found that the brain waves from the brain stem may be analyzed to provide an indication to the anesthesiologist of the changes in the patient's ability to feel pain. The anesthesia prolongs transmission through the brain stem, which may be detected by measuring the latency of evoked potential (EP) components preferably a BAER (Brainstem Auditory Evoked Response) or BSER (Brainstem Somatosensory Evoked Response).

The "latency" is the time period following the presentation of a stimulus until a particular component occurs. The interval between particular successive EP (Evoked Potential) components is especially reliable as an indicator of brainstem state, for example, the interval between Peak I, arising from the arrival at the brainstem of an incoming stimulus via the auditory nerve, and Peak IV, arising from arrival of that information at the inferior colliculus nucleus in the diencephalon, in normal persons older than 1 year, is approximately 4.0±0.2 milliseconds, which represents the time required for normal transmission through the brainstem.

Before the operation, the anesthesiologist will removably attach reference electrodes and six EEG scalp electrodes to the patient over the six main brain arteries, namely, left and right frontal, left and right center and left and right back. He/she will then administer the selected anesthesia to place the patient in the desired plane of anesthesia. At that time, measurements are made of the patient's EEG, BAER and/or BSER to provide a norm (reference or base line). Measures of vital functions such as heart rate, EKG waveshape, blood pressure, respiration and temperature may also be obtained and monitored.

In theory, the EEG system, which monitors the electrophysiology of the patient, should detect changes in the clinical state, i.e., changes in the plane of analgesia or amnesia, before there are clinical or qualitative signs of change. During the operation, the EEG system automatically and continually tests on-going EEG and challenges the patient with selected periods of stimuli to provide evoked potentials, such as BAER and BSER. These tests are automatically analyzed and are displayed. The display warns the anesthesiologist of meaningful changes in the clinical state of the patient so that he/she may take the appropriate action to restore the patient to the selected plane of anesthesia.

After the operation, the patient, preferably with the EEG electrodes still attached, is moved to the recovery room and subsequently to the intensive care unit. The EEG system now becomes part of a patient monitoring system in which the data is transmitted to a central workstation from which a nurse monitors a number of patients. Each patient has his/her own norm, which is regularly updated to track the patient's condition; a multivariate state measure; and a set of alarms if the measures fall below the criteria set by the attending physician.

DETAILED DESCRIPTION OF THE INVENTION

I. PRE-OPERATIVE PREPARATION OF THE PATIENT

Figure 1:
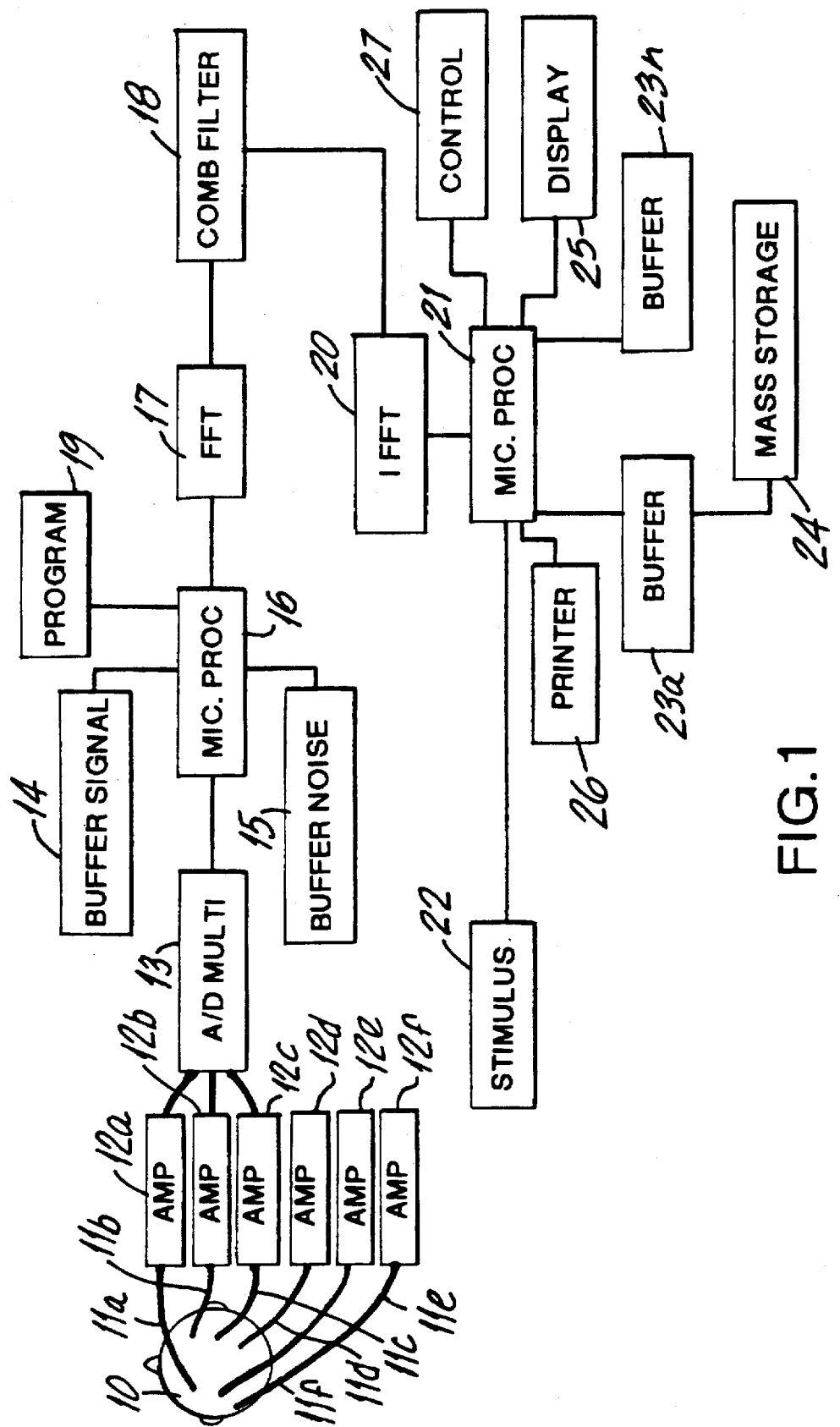
FIG. 1 is a block schematic drawing of the apparatus of the present invention.

In accordance with the present invention, the patient is prepared prior to a surgical operation. A series of EEG electrodes are removably secured to the scalp of the patient. Preferably six EEG electrodes are used in the following locations: front left ($F_3$), front right ($F_4$), center left ($C_3$), center right ($C_4$), back left ($P_3$) and back right ($P_4$). The capital letters F,C,P refer to position location names in the International 10/20 Electrode Placement System. In addition, two reference electrodes are linked and are removably positioned on the patient's mastoids, or other suitable location, to use as a reference for monopolar recording. A conventional EKG (electrocardiogram) electrode, which may be placed on the shoulder or chest, is used as ground.

The electrodes preferably use a standard electrolyte gel for contact so that the impedances of each electrode-skin contact is below 5000 ohms. The EEG system, described below, checks the electrode-skin impedance at each electrode and displays a warning if any such impedance falls below 5000 ohms.

The anesthesiologist then administers the selected anesthetics to cause the patient to attain the selected plane of anesthesia, as determined by the judgment of the anesthesiologist. That determination is made by the anesthesiologist viewing the patient's blood pressure, respiration, eye pupil dilation and other clinical signals.

A skilled EEG system operator, who may be other than the anesthesiologist, then collects a set of artifact-free EEG and BAER and BSER samples. Alternatively, data acquisition may be automatic with computer removal or exclusion of artifacts by regression or other techniques. The baseline session contains 60 seconds of EEG and EPs averaged using 2048 stimuli. The EEG system then subjects the data to spectral analysis using FFT (Fast Fourier Transform) and EP peak detection. Mean values and standard deviations are obtained for absolute ($uv^2$) and relative (%) power in the delta (1.5–3.5 Hz), theta (3.5–7.5 Hz), alpha (7.5–12.5 Hz) and beta (12.5–25 Hz) frequency bands. The PI—PV latency interval for the BAER, and the dorsal column nucleus (PA) to somatosensory cortex (PV) latency interval for the BSER (central conduction time—"CCT").

At regular intervals (approximately 5 minutes) after this baseline is established, or upon operator demand, a statistically adequate EEG and EP sample is automatically acquired, statistically compared to the baseline, and any significant deviation detected to activate a visual or auditory alarm.

II. THE INTER-OPERATIVE EEG SYSTEM

As shown in FIG. 1, the patient's head 10 is connected with the desired number of electrodes 11a–11f, preferably silver-silver chloride disk electrodes or less preferably needle electrodes. The drawing shows six electrodes. When surgical conditions restrict access to some regions of the head, one active electrode may be located at the vertex or on the forehead and reference electrodes behind the ears.

The electrodes 11a–11f are connected to respective amplifiers, each electrode lead being connected to its own amplifier. Each amplifier 12a–12f has an input isolation switch, such as a photo-diode and LED coupler, to prevent current leakage to the patient. The amplifiers 12a–12f are high-gain low-noise amplifiers, preferably having a frequency range of 0.5 to 100 Hz, gain of 10,000 common mode rejection of 100 dB and noise of less than 1 microvolts peak-to-peak.

The amplifiers 12a–12f are connected to an analog-to-digital multiplexer 13 (A/D multiplexer). The multiplexer 13 samples the amplified analog brain waves at a rate compatible with the bandwidth of the amplifiers. The multiplexer 13 provides, at its output, sets of digital data, representing the EEG input analog signals. The multiplexer 13 is connected to "buffer signal" 14, which stores the signal, and "buffer noise". 15, which stores the noise. The buffers 14,15 are connected, and A/D multiplexer is directly connected, to the dedicated microprocessor 16. For example, the microprocessor may be an Intel 386 or Intel 486. The dedicated microprocessor 16 is connected through its dedicated 512-point FFT 17 (Fast Fourier Transform) to digital comb filter 18 and is controlled by program 19.

The comb filter is connected to, and controls, the IFFT 20 (Inverse Fast Fourier Transform). The output of IFFT 20 is connected to the system microprocessor 21 (which may be Intel 386 or Intel 486) which is connected to the stimulus devices 22 (lights, loudspeaker, shock device, etc.) to the system digital storage buffers 23a–23n (only two being shown), to the mass storage 24, such as a hard disk, to the display 25, such as a CRT, and a print-out printer 26 and to the control panel 27.

The digital comb filter 18 may be as described in U.S. Pat. No. 4,705,049, incorporated by reference herein. The comb filter may be considered a series of band pass and band stop filters arranged to be responsive over a selected range. The selected range is 0–1400 Hz and there are band pass filters at 10–580 Hz, 600–640 Hz and 720–800 Hz and 900–1400 Hz and bandstop filters at 0–100 Hz, 580–600 Hz, 640–72.0 Hz, 800–900 Hz and above 1400 Hz. The band pass filters are the "teeth" of the comb and they are selected so as to accord with the frequencies in which the signal/noise ratio is acceptable. The band-stop filters are selected to be at frequencies in which the noise is excessive. The multiplexer is programmed by programmer 24, which may be obtained from a floppy disk, to obtain samples of the signal and of the noise. The noise is preferably obtained when there is an absence of evoked potential stimuli and the signal is obtained during epochs up to 600 milliseconds long, beginning with presentation of the stimuli or after a pre-selected delay.

The program and its controlled microprocessor condition the input signals and insure that they are valid biological signals. Such validity checks on the input signals include calibration measurement, impedance measurements and automatic artifact rejection algorithms.

The microprocessor 21 automatically provides a timed set of stimuli from stimulator 22 which may be an audio sound from a speaker, a visual signal from a light flash, or a tactile signal from an electric shock or a vibrator. Visual flashes may be delivered using LED goggles flashing at a rate of 1/second (VEP). Auditory clicks, about 100 db SPL, may be delivered through a stethoscope earpiece by air conduction tubes from a magnetic speaker. The rate of stimulus is preferably 7–50/second and most preferably 35–45/second, i.e., a 40 Hz auditory steady-state response (40 Hz-A55R). Common clocks and rare flashes can be combined into a randomly mixed stimulus sequence, with the EP elicited by the rare stimulus providing the cognitive "event-related potential", P300 (P3). The patient's brain will respond to these stimuli providing "Evoked Potentials" (EP) which are averaged to reduce noise, providing an "Average Evoked Response" (AER). Sample size varies with stimulus mobility, ranging from 100 (VEP) to 512–2048 (BAER/BSER).

The AER is the sum of samples time-locked to the onset of the stimuli divided by the number of samples, to provide an updated average.

III. INTRA-OPERATIVE PATIENT MONITORING

During the surgical operation, the patient is kept on the EEG system of FIG. 1, or re-connected to the system if for some reason there is an interruption.

The objective of the EEG monitoring is to provide the anesthesiologist with sufficient information regarding the state of the patient's brain to maintain the patient at the selected plane of anesthesia.

In general, this involves the intermittent collection of periodic artifact-free on-going EEG sessions, and evoked potential challenges, such as BAER/BSER, for as long as the operation lasts, the collection and analysis of the data and comparisons of features extracted from that data to the norm (the pre-operative anesthetized state of the patient) and to the baseline after induction of anesthesia.

The preferred list of measures (features) extracted by FFT is as follows: For each of the six electrodes; 5 bands of absolute power (total, delta, theta, alpha, beta), 5 bands of relative power (delta, theta, alpha, beta), for the three pairs of homologous electrodes; coherence of the total EEG and delta, theta, alpha, beta). This is a total of 84 univariate features for the on-going EEG. An overall multivariate measure of deviation, such as a mamalanobis distance, is compared for each lead and across the six leads, 7 more EEG features.

In addition to the collection and analysis of on-going EEG, discussed above, the patient is automatically subjected to suitable stimuli at selected intervals over the course of the operation to provide sets of EPs (Evoked Potentials).

The brain stem auditory evoked response (BAER) has, in normal subjects, 5 peaks. These latencies are expressed as milliseconds from the stimuli and are closely similar in shape and latency across neurologically normal persons. The time shift of certain of these latencies, and their suppression, is proportional to the patient's response to anesthesia. The first 5 positive peaks, in response to click (auditory) stimulus, are believed to reflect the successive activation of the acoustic nerve, cochlear nucleus, superior olivary complex, lateral lemniscus and inferior colliculus. The Peak I–Peak V latency interval is probably the preferred BAER indicator to use. Another useful indication of the patient's state is the brain stem somatosensory evoked response (BSER). It is believed that the successive peak latencies reflect, in order, the activation of the dorsal column nuclei, medial lemniscus, thalamus, sensory radiation and the first cortical synapses. The PA–PI latency interval (CCT) is probably the preferred indicator to use.

The feature extraction method for VEPs or P300 involves alternative ways to describe EP signal strength, variability, and interhemispheric symmetry. These features are extracted for latency domains: 80–200 and 200–500 msec. Measures of signal strength ("features") include absolute peak-to-peak (p-p) amplitude and "normalized" p-p amplitude. Normalized p-p amplitude is obtained by defining the largest amplitude as 100%, and other measurements are scaled relative to that maximum. Measures of EP variability include the standard deviation of the p-p amplitude (s), the variance ($s^2$), and log variance (log $s^2$). The standard deviation of the p-p amplitude (s) is an rms measure: rms=$(s_{Pmax})^2+(s_{Pmin})^2$, where s is the standard deviation, and $_{Pmax}$ and $_{Pmin}$ are the largest positive and largest negative peaks, respectively, within a particular latency domain (100–250 msec or 250–500 msec). Log $s^2$ is computed because $s^2$ itself is not normally distributed. A measure of signal-to-noise ratio (S/N) is computed as well, where "signal" is the p-p amplitude, and "noise" is its standard deviation. The principal measure of bilateral EP symmetry is the Pearson product-moment correlation (r) across the time bins, computed for EPs recorded from homologous derivations in left and right hemispheres ($C_3$ vs. $C_4$, $F_3$ vs. $F_4$ and $P_3$ vs. $P_4$, etc.), and referred to as "interhemispheric coherence". The square of the product-moment correlation coefficient ($r^2$) is also obtained for each homologous pair of derivations. Across the set of six electrodes, there are thus 91 quantitative EEG descriptions, 194 VEP and P300 descriptors, and two preferred brainstem EP descriptors. All of these various features are then compared against the "baseline" (data collected from the pre-operative patient after being anesthetized). As experience with anesthetic effects is accumulated, it can be expected that this large set of features will be decreased. Each measure may be z-transformed using the corresponding mean and standard deviation obtained from the baseline. Each z-score for a patient is calculated in the following manner: the reference pre-operative mean, X, for a particular measure, is subtracted from the value X for that measure obtained from the patient during the operation. The difference, X—X, is divided by the standard deviation, s, of that measure for the baseline. Thus, $z=(X-\overline{X})/s$. If the distribution of a variable is Gaussian, the z-score provides an estimate of the probability that an observed measure is "abnormal" i.e., improbable.

In addition, the patient's measures are statistically compared with a normative reference database based on measures obtained inter-operatively from a group of normal patients having successful outcomes of specific surgical procedures using specific anesthetic materials. For example, a database is obtained on the surgical procedure of a prostate operation in a normal group of patients using the gas halothane. Further, the patient's measures are statistically compared to a normative reference database based on measures taken from a normal group having post-operative reports of successful operative administration of anesthesia, regardless of the operative procedure.

Alternatively, measures may be assessed by computing sensitive indices such as $$\frac{\text{delta plus theta}}{\text{alpha plus beta}} \text{ or } \frac{\text{theta}}{\text{alpha}}$$

and calculating the ratio of such combined variables or of univariate measures if successive samples of EEG/EP relative to baseline values. Another alternative to the Z-transform is to use the F-ratio derived from the variance within the samples divided by the variance of the baseline. Statistically significant thresholds can be defined for each of these alternatives.

Figure 2A:
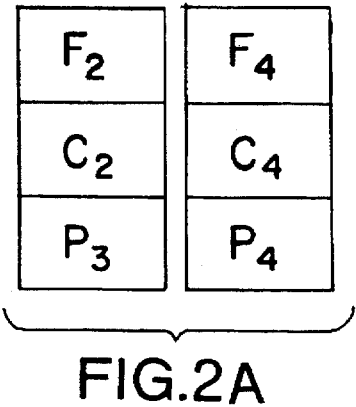
FIG. 2A is a diagram of a display showing the corresponding position in the display for each electrode.

The system will combine measures, after having Z-transformed them relative to the baseline, and display the combinations as "trajectories". Upper and lower alarm limits can be separately adjusted. The screen, as shown in FIG. 2A, will show six trajectories (vectors) corresponding in location to the six EEG electrodes, plus one trajectory for every EP category. It is conceivable that, in view of future knowledge about such monitoring, selected measures may be used to achieve feedback control of anesthetics.

Figure 4:
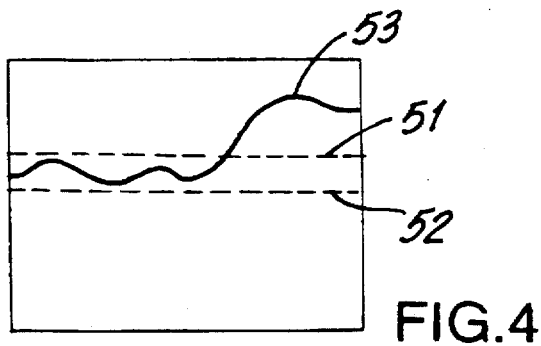
FIG. 4 is a display of a trajectory of the patient's state as measured at one electrode.

As shown in FIG. 4, which is an enlargement of one of the six scales of FIG. 2A, the baseline is defined as a mean 50. The upper and lower confidence intervals of 2.5 standard deviations from the mean are shown as lines 51 and 52. Any excursion of the trajectory 53 beyond the normal band, defined by lines 51 and 52, is "abnormal" and will trigger a warning signal, such as a flashing light or buzzer or a vibratory signal on a wrist band worn by the operator.

Figure 2B:
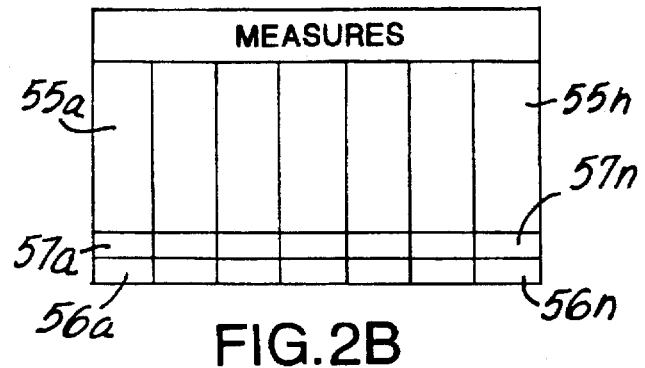
FIG. 2B is a display of the measures at one electrode.

An alternative display is shown in FIG. 2B, which shows a moving chart (histogram) type of display. That display will be shown individually for each of the 6 electrodes, either on the same screen or in sequence. Each measure (feature) has its own column 55a–55n. The latest result of each measure is color coded, preferably using a "heat" color scale, and shown as a bar 56a–56n on the bottom of each column. The prior measure result is moved upward (scrolled up) and becomes the bar 57a–57n. In this way changes in each measure, at each electrode, may be displayed. The bars will change (scroll upward) with every update of the assessment, at intervals which will depend upon data variance, the full set of data being monitored, and ambient electrical noise levels and may range from 5 to 120 seconds for different EEG and EP measures.

IV. THE RECOVERY ROOM/ICU EEG SYSTEM

Figure 3:
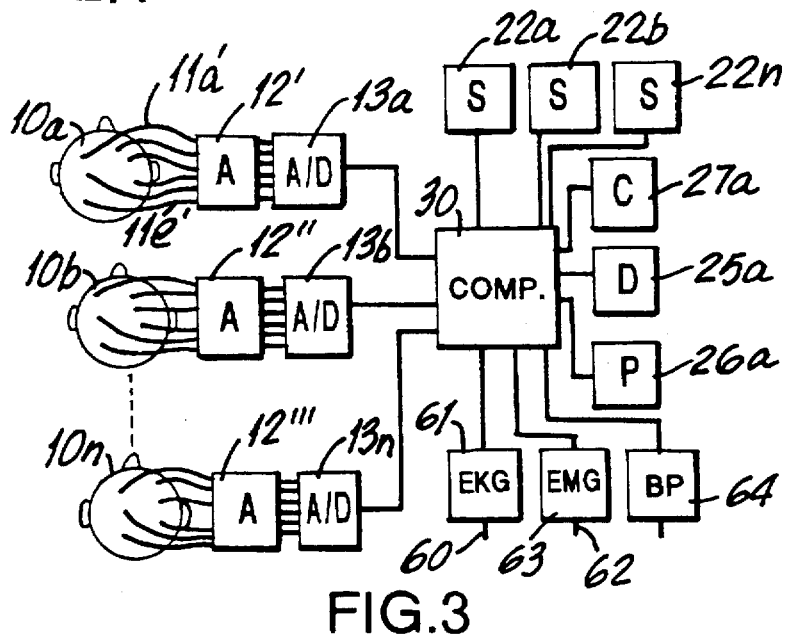
FIG. 3 is a block schematic drawing of another embodiment of the apparatus of the present invention.

As shown in FIG. 3, a multi-patient monitoring system is used in the recovery room and the intensive care unit (ICU). It consists of six electrodes 11a'–11e' removably connected to the head 10a–10n of each patient, i.e., 24 electrodes for a 4-patient system. As in the embodiment of FIG. 1, each electrode is connected to an amplifier (the group of 6 amplifiers shown as 12'–12''') and the amplifiers connected to an analog-to-digital multiplexer 13a–13n. The computer 30 includes the buffer signal, buffer noise, dedicated microprocessor, FFT, digital comb filter, IFFT, system microprocessor, stimulus device control for a stimulus device 31a–31n for each patient, storage buffers and mass storage as in the FIG. 1 apparatus. The computer 30 is connected to control panel 27a and the computer is connected to and controls display 25 and printer 26a. In the embodiment of FIG. 3, the "raw" digital data from each patient is transmitted to central computer 30. Alternatively, each patient station may have an "on-board" computer, so that only the changes in the patient's state would be transmitted to the central computer 30.

A nurse or doctor is able to monitor a number of patients by watching a single windowed display, for example, on a video monitor. For example, each minute the trajectory from a different patient, in order, might be displayed, or a different critical measure from the patients in each bed might be updated on their trajectories.

Each patient is also connected to a set of EKG (electrocardiogram) electrodes 60 to detect changes in EKG waveshape and rate of heart activity and to EMG (electromyograph) electrodes 62 to detect muscle activity, to a blood pressure detector 64 (sphygmomanometer) to measure systolic, diastolic and pulse pressure, to sensors or respiration, expired $CO^2/O_2$ and body temperature. The EKG amplifier 61 and the EMG amplifier 63 and blood pressure device 64, respiration and temperature sensors, are connected to the computer system 30 and may be of conventional construction. These measures are similarly updated on vital sign trajectories.

In the recovery room or ICU, the doctor will monitor the patient and obtain a new self-norm for the patient at each stage of recovery. For example, in the recovery room as the muscle paralysis is lessened and the patient starts to become conscious a new self-norm is obtained. If the patient then regresses, the new self-norm will provide the statistical basis for the warning signal of the regression. Trajectories can be plotted against individual self-norms for most sensitive detection of clinically significant fluctuations within each patient, against population norms to assess deviation from normal healthy persons, or against group average values constructed against some reference group of patients (e.g., "good" versus "bad" outcomes). Note that diurnal rhythms related to sleep cycles may require time-dependent changes in threshold definitions for alarms, e.g., theta power increases with drowsiness.

In the ICU the data from bedside amplifiers attached to all the monitored patients are transmitted to the nursing workstation, which includes multiplexed analysis capabilities in the computer 30 and display 25a. Regularly updating trajectories with alarms help nursing staff monitor each patient. When significant change occurs, a new set of data as the patient's current self-norm.

Figure 5:
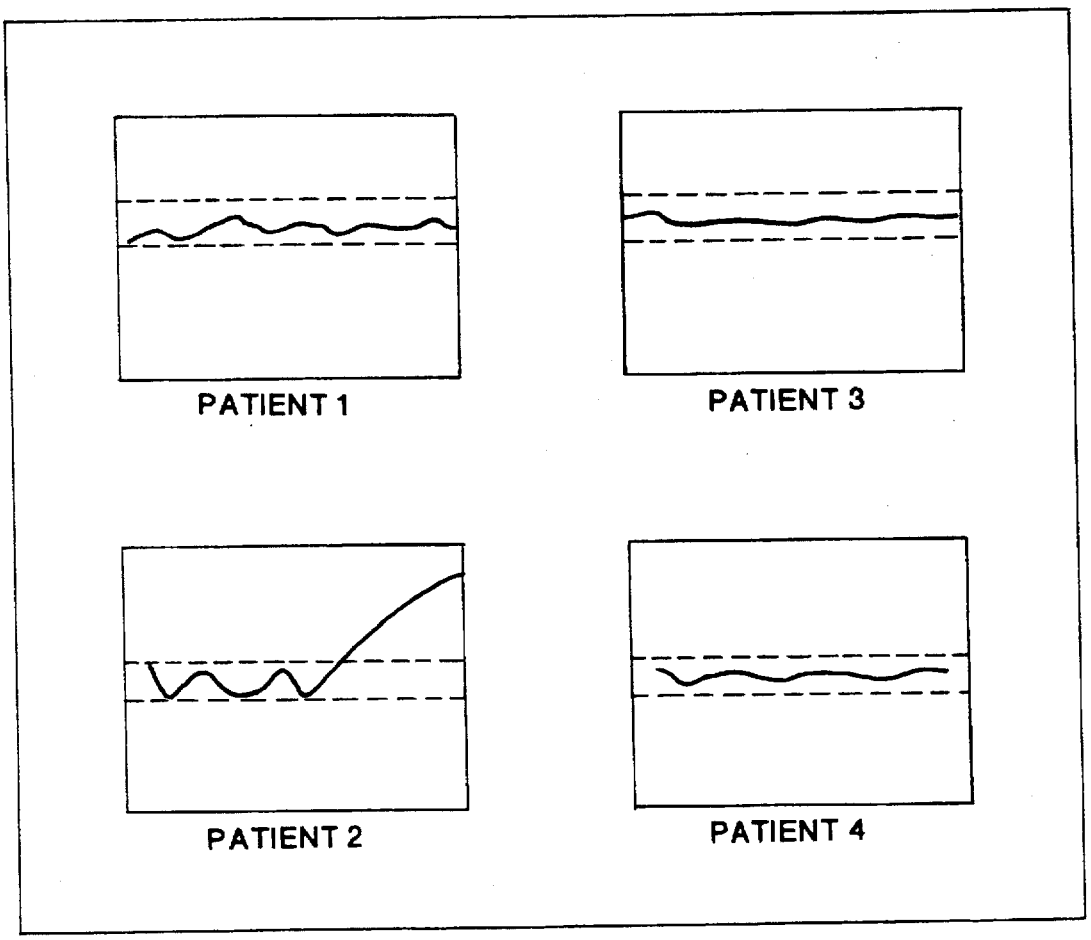
FIG. 5 is an illustration of a display for the system of FIG. 3.

The information from the EEG may be combined with the EKG and other vital sign data to provide a multi-variate overall state measure. If any constituent measure or the overall state becomes abnormal, for example, more than 2.5 or 3 standard deviations from the mean, then the alarm warning is sounded. The multi-variate measure, as shown in FIG. 5, is shown as a trajectory between the normal lines 61 and 62 for each patient, on the screen of the display 25a. This composite, or univariate trajectories, may be printed out, on a regular basis, by printer 26a. Preferably, the display 25a is a multi-window display on a video monitor in which the state of each patient is simultaneously shown in a window of the display.

Other embodiments are within the scope of the claims. For example, in the embodiment described above, the anesthesiologist uses his own judgment to select the proper plane of anesthesia. Early in the use of the present invention this, indeed, will be the case. However, after a database has been established, which comprises both the data form the operation and subsequent patient outcomes, the monitoring system of the present invention may play a greater role in suggesting the proper level of anesthesia. Alternatively, because various anesthesiologists may differ in their preference of anesthetics or level of anesthesia, an additional database which stores only the cases from one anesthesiologist may be relied upon. One method by which the monitor may suggest the proper level is to create a ratio which compares the pre-anesthesia baseline to the present level of anesthesia utilizing a variable such as PI–PV, the latency of P300, or other EP component. Ratios based on BSER or BSSER, or other such physiological measures or frequency distribution of the EEG or other type of statistical analysis of these measures may also be used. This ratio might be termed a c/u ratio (consciousness/unconsciousness ratio) rather than "consciousness meter" because the latter term suggests that one can say something about levels of consciousness based on this ratio which has not been proven scientifically.

What is claimed is:

1. A method for simultaneously monitoring a plurality of patients comprising:

(a) removably connecting a set of EEG electrodes to the scalp of each patient and a set of EKG electrodes and a blood pressure sensor to the body of each patient;

(b) presenting a set of stimuli to each patient and amplifying and digitizing the brain wave evoked responses to the stimuli and the patient's ongoing brain wave activity collected from the EEG electrodes to provide a first set of EEG, EKG and blood pressure digital data representing each patient's brain waves, heart activity and blood pressure in the patient's first state and recording the first set of digital data in computer system memory;

(c) subsequently presenting the same set of stimuli to each patient and amplifying and digitizing the brain wave responses to the stimuli and the patient's on-going brain wave activity and heart activity and blood pressure to provide a second set of digital data for each patient;

(d) using the computer system to statistically compare the first and second sets of digital data for each patient on a feature-by-feature basis and providing a warning if a combined multi-variant measure is abnormal by being of a difference between the first and second sets of digital data larger than a selected range of differences.

2. The method of claim 1 wherein the stimuli are auditory and the evoked responses are brain stem auditory responses (Brainstem Auditory Evoked Response).

3. The method of claim 1 wherein the stimuli are electrical or tactile and the evoked responses are brainstem somatosensory evoked responses (BSER).

4. The method of claim 1 wherein a plurality of electrodes are employed.

5. The method of claim 1 wherein the measures of the ongoing EEG include absolute and relative power in the delta, theta, alpha and beta bands.

6. The method of claim 1 wherein the warning is a visual signal on a computer system monitor screen or a toner signal.

7. The method of claim 1 wherein the statistical comparison for each patient is shown as a window on a video monitor display.

* * * * *